United States Patent [19]
Goudie et al.

[11] 4,243,682
[45] Jan. 6, 1981

[54] FLUORONAPHTHYLONES

[75] Inventors: Alexander C. Goudie, Harlow; Laramie M. Gaster, Sawbridgeworth, both of England

[73] Assignee: Beecham Group Limited, England

[21] Appl. No.: 953,465

[22] Filed: Oct. 23, 1978

[30] Foreign Application Priority Data

Nov. 3, 1977 [GB] United Kingdom ............... 45712/77

[51] Int. Cl.$^3$ ...................... A01N 35/00; C07C 49/23
[52] U.S. Cl. .................................. 424/331; 260/340.7; 568/633; 568/659; 568/660; 568/661; 560/255; 560/221; 560/73; 560/76; 560/55; 560/72; 560/19; 560/59; 568/808; 424/311; 424/343; 424/327; 424/340; 424/341; 424/278; 260/340.9 R; 568/328; 568/39
[58] Field of Search ........ 260/590 D, 590 R, 590 FA; 568/808, 659, 661, 660; 560/255; 424/331, 311, 343, 327, 340, 341

[56] References Cited

U.S. PATENT DOCUMENTS 4,035,406  7/1977  Anderson et al. .................... 560/255
4,081,476  3/1978  Anderson et al. .................... 560/255

FOREIGN PATENT DOCUMENTS 1474377  11/1976  United Kingdom ............. 260/590 FA

OTHER PUBLICATIONS

Abe et al., Chem. Abst., vol. 74, #140843e, (1971).

Primary Examiner—James H. Reamer
Attorney, Agent, or Firm—Jacobs & Jacobs

[57] ABSTRACT 4-(6-Substituted naphthyl)butan-2-ols,-butan-2-ones,-pentan-2-ols and -pentan-2-ones bearing a fluoro group in the naphthyl ring, and pro-drugs thereof, are anti-inflammatory agents. A typical embodiment is 4-(4-fluoro-6-methoxy-2-naphthyl)-butan-2-one.

8 Claims, No Drawings

FLUORONAPHTHYLONES

DETAILED DISCLOSURE

The present invention relates to naphthalene derivatives, to their preparation and to compositions containing them.

British Pat. No. 1,474,377 discloses the anti-inflammatory effectiveness of the compounds of the formula (I):

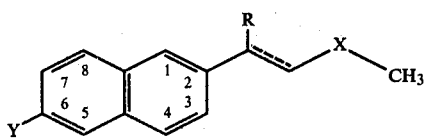

wherein R is a hydrogen atom or a methyl group, X is a CO or CHOH group, Y is a chlorine or bromine atom or a $C_{1-4}$ alkyl, methoxyl or methylthio group and the dotted line represents a double bond optionally present. It has now been discovered that if the ring carrying the substituted butyl side chain is substituted by a fluorine atom then the resulting compounds have an enhanced anti-inflammatory effectiveness, for example as judged on the 'Cotton Pellet Test'.

Accordingly the present invention provides the compounds of the formula (II):

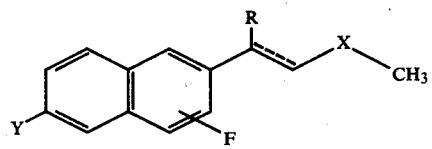

and pro-drugs therefore wherein R, X and Y are as defined in relation to formula (I) and F is the 1- or 4-position.

Those compounds wherein X is a CHOH group may be in the form of an isolated optical isomer or may be presented as mixtures of such isomers, for example the R, S, or RS forms may be used.

When used herein the term 'pro-drug' means a compound metabolised in-vivo to a compound of the formula (II). The pro-drugs will be derivatives of the group X, for example those wherein the 2- position side chain is the sub-formulae (a)-(d):

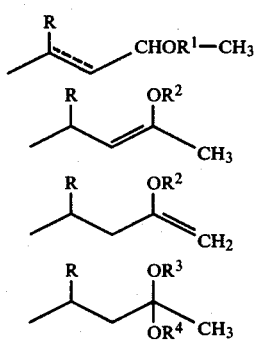

wherein R is hydrogen atom or a methyl group, $R^1$ is a group $CO.R_5$ wherein $R_5$ is the residue of a pharmaceutically acceptable carboxylic acid of up to 9 carbon atoms of the formula $R_5.CO.OH$; $R^2$ is a $C_{1-4}$ alkyl group or a $CO.R_5$ group; $R^3$ is methyl, ethyl or propyl group and $R^4$ is a methyl, ethyl or propyl group or is joined to $R^3$ so that $R^3$ or $R^4$ together represent a $CH_2CH_2$ or $CH_2CH_2CH_2$ group.

Suitable groups $R_5$ include alkyl, alkenyl, aralkyl or the like group optionally substituted by hydroxyl, acyloxy, alkoxyl, carboxamido, optionally salted carboxyl or amino, acylamino, alkylamino, dialkylamino or the like.

Particularly suitable groups $R_5$ include the phenyl group, alkyl groups of 1-4 carbon atoms, alkyl groups of 1-4 carbon atoms substituted by a phenyl group or one the aforenamed substituted by hydroxyl, acetoxyl, methoxyl, acetamido, salted amino, amino, $C_{1-4}$ alkylamino, di-$C_{1-4}$-alkylamino, carboxyl, salted carboxyl or the like group.

Particularly suitable groups $R_5$ include the methyl, ethyl, n-propyl, iso-propyl, t-butyl, phenyl, benzyl, phenylethyl, acetoxymethyl, methoxymethyl, hydroxymethyl, optionally salted aminomethyl, 2-acetoxyphenyl, 4-methoxyphenyl, 3,4-dimethoxyphenyl, 3,4,5-trimethoxyphenyl, or the like group.

Preferred groups $R_5$ include the methyl, ethyl, benzyl, 2-methoxyphenyl, phenyl and 3,4,5-trimethoxyphenyl groups.

The compounds possessing a group of the sub-formula (a) possess a chiral centre at C-2. Such compounds may be as an isolated optical isomer or mixtures of such isomers e.g. the R,S, or SR form. Often the S- form is preferred.

Particularly suitable groups $R^2$ include the methyl, ethyl, propyl, butyl, acetyl, propionyl, butionyl, benzoyl and the like.

Preferably $R^2$ is an ethyl, acetyl or propionyl group.

Particularly suitable values for $R^3$ include the ethyl and propyl groups.

Preferred groups $R^3$ include the ethyl group.

Particularly suitable values for $R^4$ include the ethyl and propyl groups.

Preferred groups $R^4$ include the ethyl group.

A particularly suitable value for Y is the chlorine atom.

A further particularly suitable value for Y is the methyl group.

A preferred value for Y is the methoxyl group. Thus certain favoured compounds of this invention are of the formula (III):

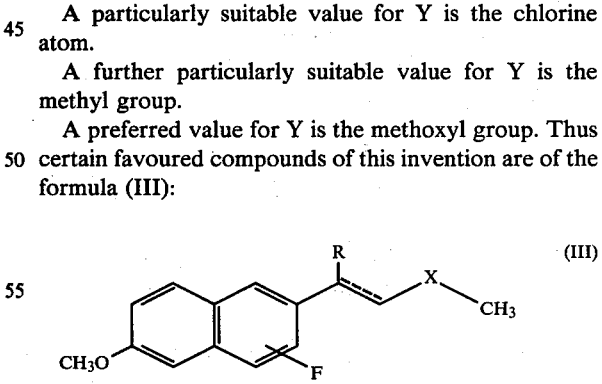

wherein R, X and the dotted line are as defined in relation to formula (I).

Most suitably R in the preceding formulae is a hydrogen atom as this is expected to reduce or remove any of the slight oestrogenicity which might be associated with corresponding compounds wherein R is a methyl group. Thus certain favoured compounds of this invention are those of the formula (IV):

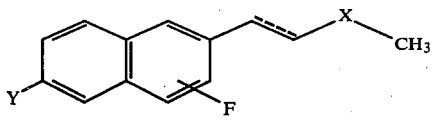

wherein X, Y and the dotted line are as defined in relation to formula (I).

Most suitably the dotted line in the preceding formulae does not represent the optional double bond as this is expected to reduce or remove any of the slight oestrogenicity which might be associated with the corresponding double bonded compounds. Thus certain favoured compounds of this invention are those of the formula (V):

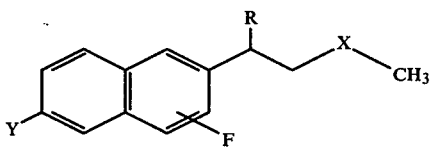

wherein R, X and Y are as defined in relation to formula (I).

From the foregoing it will be realised that certain favoured compounds of this invention are those of the formula (VI):

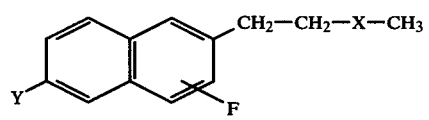

wherein X and Y are as defined in relation to formula (I).

Yet another group of favoured compounds is that of the formula (VII):

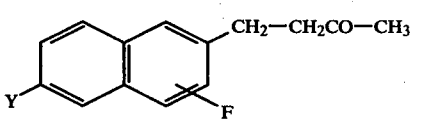

wherein Y and F are as defined in relation to formula (II).

The fluorine atom in the preceding compounds of the formulae (II)–(VI) may be in the 1- position.

Most suitably the fluorine atom in the preceding compounds is in the 4-position.

From the foregoing it will be realised that certain particularly suitable compounds of this invention are those of the formula (VIII):

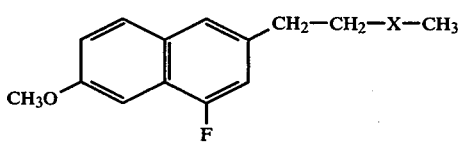

and pro-drugs therefor wherein X is as defined in relation to formula (I).

Particularly suitable compounds of the formulae (II)–(V) include those wherein X is a CO group.

Compounds according to this invention include:
4-(4'-fluoro-6'-methoxy-2'-naphthyl)butan-2-one;
4-(4'-fluoro-6'-methoxy-2'-naphthyl)butan-2-ol:
4-(4'-fluoro-6'-methyl-2'-naphthyl)butan-2-one;
4-(4'-fluoro-6'-methyl-2'-naphthyl)butan-2-ol;
4-(4'-fluoro-6'-methoxy-2'-naphthyl)pentan-2-one;
4-(4'-fluoro-6'-methoxy-2'-naphthyl)pentan-2-ol;
4(4'-fluoro-6'-methoxy-2'-naphthyl(pen-3-en-2-one.

Yet another compound according to this invention is:
4-(1'-fluoro-6'-methoxy-2'-naphthyl)butan-2-one.

The present invention also provides a pharmaceutical composition which comprises a compound of the formula (II) or a pro-drug therefore and a pharmaceutically acceptable carrier.

The compositions of this invention may be formulated for oral, injection, topical or suppository administration but normally and preferably the composition will be formulated for oral administration.

The unit dosage form of the composition of this invention will generally contain from 20 mg to 1000 mg of the active ingredient and more usually from 50 mg to 600 mg, for example about 75, 100, 150, 200, 250, 300, 400, 500 or 600 mg.

The compositions of this invention are normally administered more than once a day, for example 2, 3, 4, 5 or 6 times per day in such a manner that the total daily dose of the active ingredient is generally from 100 mg to 2500 mg per day and usually from 200 mg to 1800 mg per day, for example about 300, 400, 500, 600, 700, 800, 900, 1000, 1200, 1500 or 1800 mg per day.

The compositions of this invention may be employed as anti-inflammatories and/or analgesics for example in the treatment of rheumatic and arthritic diseases.

The compositions may be formulated in conventional manner and may contain agents such as disintegrants, binders, fillers, flavouring agents, glidants, lubricants, colouring agents and the like. The compositions may be prepared by conventional methods of mixing, filling, compressing or the like, for example in similar manner to known anti-inflammatory agents such as ketoprofen, phenoprofen, acetylsalicyclic acid, naproxen or the like.

A favoured form of the composition of this invention is a hard gelatin capsule containing the active agent. The active agent may be in the form of a powder, granulate or the like and may advantageously be in intimate mixture with a lubricant such as magnesium stearate.

A further favoured form of the composition of this invention is a tablet containing the active agent. The active agent may be in the form of a recompressed granulate of the active ingredient in intimate mixture with a lubricant such as magnesium stearate, a filler such as microcrystalline cellulose and a disintegrant such as sodium starch glycollate.

The compounds of the formula (II) may be prepared by the processes outlined in the following Schemes 1, 2 and 3:

Scheme 1
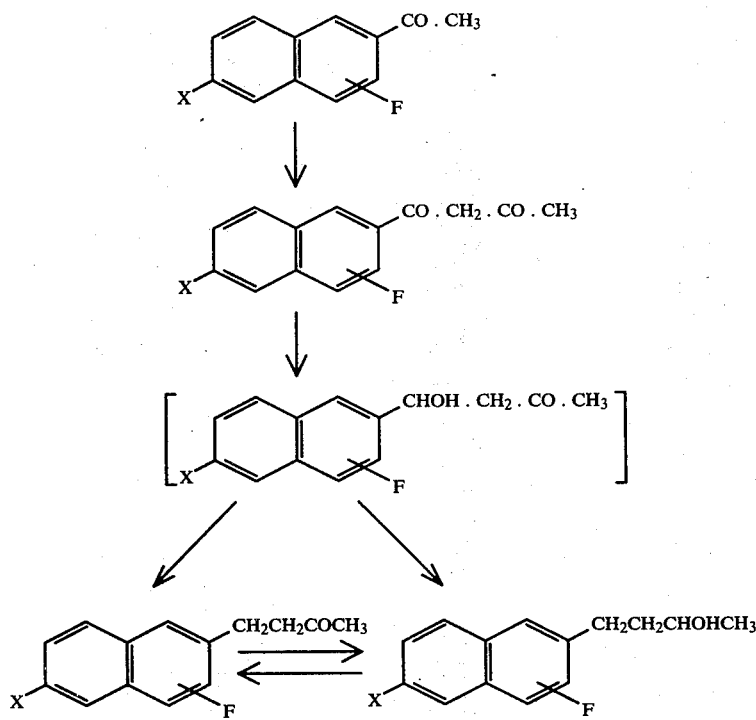
Scheme 2
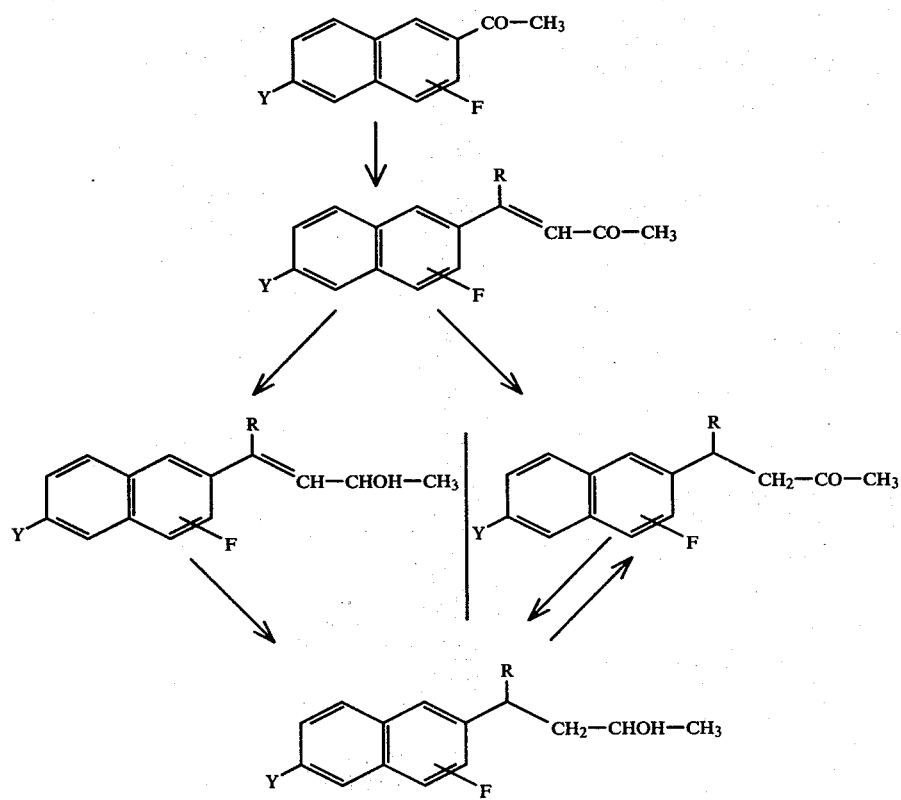

Scheme 3

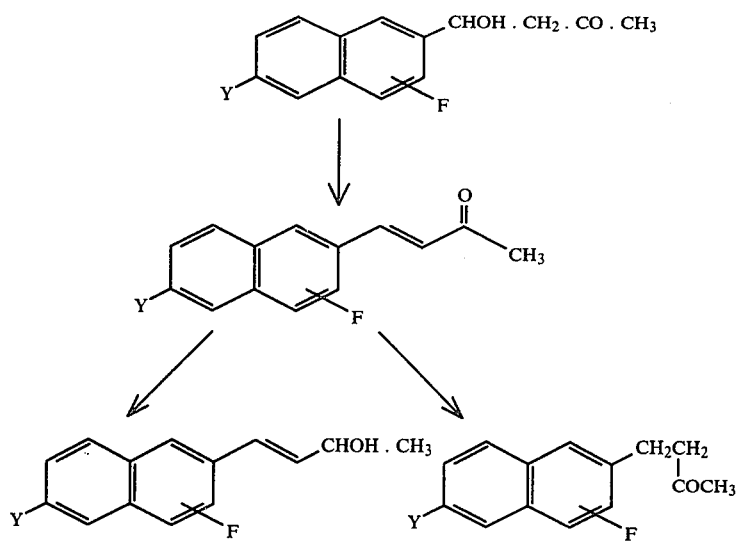

Scheme 4

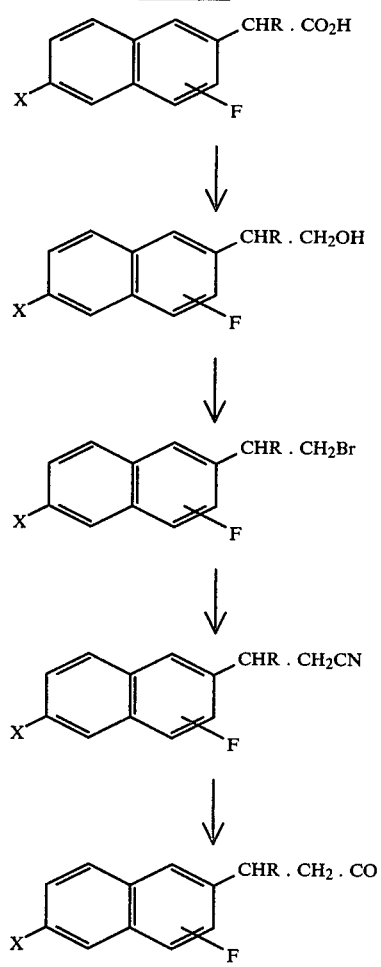

The present invention provides a process for the preparation of the compounds of the formula (II) as hereinbefore defined wherein the dotted line does not represent a double bond, X is CO and R is a hydrogen atom which comprises the catalytic reduction of a compound of the formula (IX):

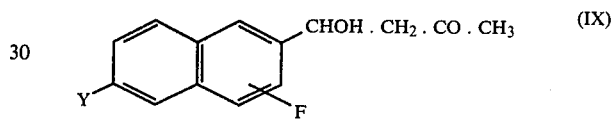

wherein Y is as defined in relation to formula (II).

The reduction may employ a low, medium or elevated pressure of hydrogen. A pressure of 1-4 atmospheres is generally suitable and a slightly super-atmospheric pressure of hydrogen is convenient.

The catalyst used for the reduction will normally be a transition metal catalyst such as palladium, for example palladium on charcoal or on some similar support.

The reduction may be carried out in a conventional reduction solvent such as glacial acetic acid, tetrahydrofuran or ethanol or with perchloric acid in ethyl acetate.

This process is generally not preferred when Y represents a bromine atom.

The present invention also provides a process for the preparation of a compound of the formula (IX) which comprises the catalytic reduction of a compound of the formula (X):

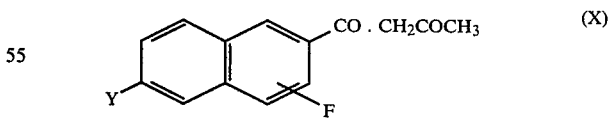

wherein Y is as defined in relation to formula (II).

The reduction of the formula (X) may be reduced under similar conditions to those used to reduce the compound of the formula (IX).

From the foregoing it is apparent that reduction of the compound of the formula (X) may be utilized for the preparation of the compounds of the formula (II) wherein the dotted line does not represent a double bond, X is CO and R is a hydrogen atom by using a longer reaction time. This is often a particularly convenient method of preparing the compounds of the formula (VIII).

This invention also comprises a process for the preparation of a compound of the formula (II) wherein the dotted line represents a double bond which process comprises the acid catalysed elimination of the elements of H₂O from a compound of the formula (IX) as hereinbefore defined.

The elimination may be brought about by heating a solution of the compound of the formula (IX) in an inert solvent such as benzene or toluene in the presence of a catalytic amount of a dehydrating agent such as paratoluenesulphonic acid or the like.

In a further aspect the present invention provides a process for the preparation of a compound of the formula (XI):

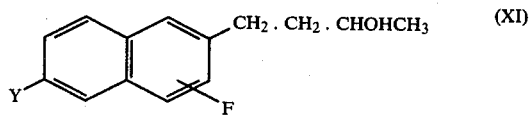

which process comprises the reduction of a compound of the formula (XII):

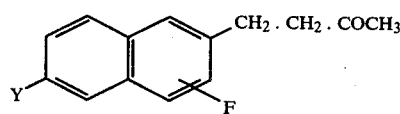

The reduction of the compound of the formula (XII) may be brought about by the action of a complex metal hydride such as sodium borohydride, lithium aluminium hydride or the like. Such reactions may be effected in a solvent conventionally used with such reagents and at a non-extreme temperature, for example 0° C. to 35° C., and conveniently at room temperature.

The compounds of the formula (XI) may according to this invention also be produced by the reduction under forcing hydrogenation conditions of a compound of the formulae (IX) or (X). Such reactions may employ catalysts such as platinum or platinum oxide and elevated pressures and temperatures.

In another aspect this invention provides a process for the preparation of a compound of the formula (XII) which comprises the oxidation of a compound of the formula (XI). Such oxidation may be brought about by such conventional oxidizing agents as chromium trioxide in acetone or pyridinium chloroformate in dry dichloromethane.

A favoured process according to this invention comprises a process for the preparation of a compound of the formula (XIII):

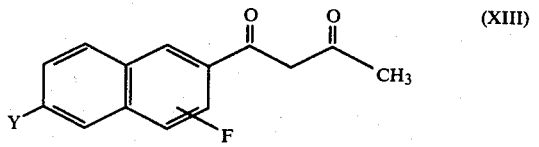

wherein Y is as defined in relation to formula (II) which process comprises the reaction of a compound of the formula (XIV):

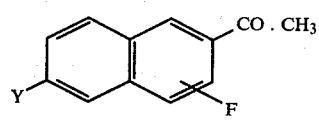

with an ester of acetic acid or acetyl chloride in the presence of a base.

The ester of acetic acid may be a lower alkyl or aralkyl or aryl ester. Convenient esters include those alkyl esters of up to 4 carbon atoms. Particularly suitable esters include methyl acetate and ethyl acetate.

The base used in this process will be one capable of removing a proton from a methyl ketone to generate the anion. Suitable bases include sodium hydride, sodium alkoxide or the like.

A preferred base is sodium hydride.

The condensation reaction will be performed in an aprotic medium such as dimethoxyethane, tetrahydrofuran, dimethylsulphoxide or the like.

The reaction is generally performed at a somewhat elevated temperature, for example 35°–65° C. and suitably 40°–55° C.

This invention also provides a process for the preparation of a compound of the formula (XV):

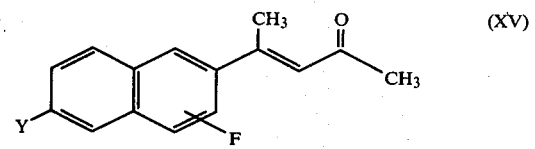

which comprises the reaction of a compound of the formula (XIV) with a Wittig reagent such as QCH₂CO₂C₂H₅ or its chemical equivalents where Q is a trialkyloxy substituted phosphorus atom followed by hydrolysis, acid chloride formation and methylation.

A suitable Wittig reagent is triethyl phosphonoacetate. The condensation may be effected in dimethoxyethane or the like. The reaction is conducted at elevated temperature.

The ethyl ester may be hydrolysed by dilute base, and the resulting carboxylic acid converted to the acid chloride with thionyl chloride or the like. Conversion to the methylketone is effected using dimethylcopperlithium at −70°−−50° C.

The compounds of the formulae (XVI), (XVII) and (XVIII):

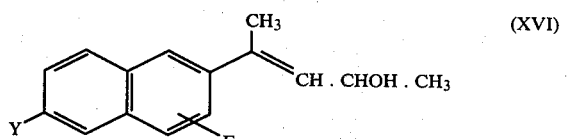

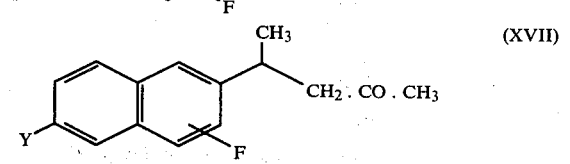

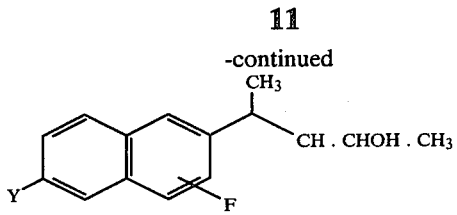 (XVIII)

may be prepared according to this invention by methods of reduction strictly analogous to those hereinbefore described from the corresponding compounds in which the α-methyl group is replaced by an α-hydrogen atom.

The conventional pro-drugs of the compounds of the formula (II) may be prepared from the compounds of the formula (II) in conventional manner.

Thus, for example, those compounds containing a side chain of the sub-formula (a) may be prepared by the acylation of a corresponding compound containing a side chain of the sub-formula (e):

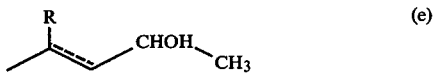 (e)

Suitable methods of acylation include those described in Belgian Pat. No. 854429.

Also, for example, those compounds containing a side chain of the sub-formulae (b), (c) or (d) may be prepared by the enol acylation or enol etherification of a corresponding compound containing a side chain of the sub-formula (f):

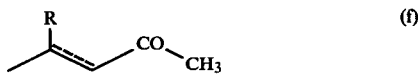 (f)

Suitable methods of enol acylation or enol etherification include those described in West German Application No. P 2647966.3.

As will be realised from the preceding, the compounds of the formula (XIX):

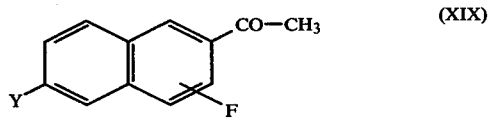 (XIX)

wherein Y is as defined in relation to formula (II) are useful intermediates and as such form part of this invention.

Most suitably Y in the compound of the formula (XIX) is a chlorine atom or a methyl group or a methoxyl group and preferably is a methoxyl group. Suitably the fluorine atom is in the 1-position. Preferably the fluorine atom is in the 4-position.

A further useful group of novel intermediates which form part of this invention are the compounds of the formula (XIII):

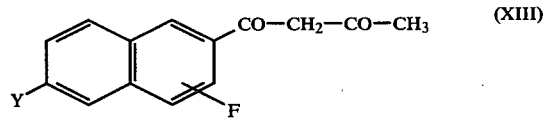 (XIII)

wherein Y is as defined in relation to formula (II).

Most suitably Y in the compound of the formula (XIII) is a chlorine atom or a methyl group or a methoxyl group and preferably is a methoxyl group. Suitably the fluorine atom is in the 1-position. Preferably the fluorine atom is in the 4-position.

This invention also provides a process for the preparation of a compound of the formula (XIX) which comprises the acetylation of a corresponding compound of the formula (XX):

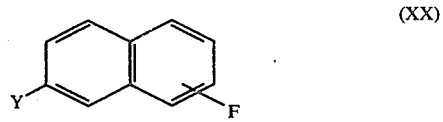 (XX)

wherein Y is as defined in relation to formula (II).

The acylation may be performed by conventional methods such as the reaction of the compound of the formula (XX) with acetyl chloride in a solvent such as nitrobenzene at ambient temperature in the presence of a Lewis acid such as aluminium trichloride.

The compounds of the formula (XX) may be obtained by the methods of Adcock and Dewar, Synthesis of Substituted α- and β-Fluoronaphthalenes, J. Amer, Chem. Soc., 89, 386 (1967).

The following Examples illustrate the invention:

EXAMPLE 1

2-Acetyl-4-fluoro-6-methoxynaphthalene

A solution of 1-fluoro-7-methoxynaphthalene (13 g, 0.074 mol) and acetyl chloride (8.01 g, 0.10 mol) in nitrobenzene (120 ml) was treated at 0° C. with powdered anhydrous aluminium chloride (15.59 g, 0.11 mol) over a period of 30 minutes. After stirring at room temperature overnight, the reaction mixture was treated with a mixture of ice (50 g) and concentrated hydrochloric acid (20 ml). The mixture was steam distilled until removal of nitrobenzene was complete. The residue was cooled and the product extracted into ether. The ether layers were washed, dried and concentrated to give a brown solid which was purified by column chromatography on silica gel using petroleum ether/ether mixture as eluant. The product was recrystallised from ether to give a coloured solid 5.33 g. m.p. 96°-7° C.

'H Nmr (CDCl$_3$)δ: 7.10–8.15 (m, 5H), 3.97 (s, 3H), 2.68 (s, 3H).

EXAMPLE 2

4-(4-Fluoro-6-methoxy-2-naphthyl)-4-hydroxy-but-3-en-2-one

A mixture of sodium hydride (0.048 mol) and ethyl acetate (4.22 g, 0.048 mol) in dry dimethoxyethane (10 ml) under nitrogen, was treated over 30 minutes at room temperature with a solution of 2-acetyl-4-fluoro-6-methoxynaphthalene (5.33 g, 0.024 mol) in dry dimethoxyethane (25 ml). The reaction mixture was then stirred at 50° C. for 3½ hours. After cooling it was treated with water (50 ml) then dilute hydrochloric acid (50 ml) and the orange precipitate collected by filtration, washed with petrol and dried. Recrystallisation from methanol/ether gave 3.2 g product m.p. 107°-8° C.

'H Nmr (CDCl$_3$)δ: 7.08–808 (m, 5H), 6.19 (s, 1H), 3.97 (s, 3H), 2.21 (s, 3H).

EXAMPLE 3

4-(4-Fluoro-6-methoxy-2-naphthyl)butan-2-one 4-(4-Fluoro-6-methoxy-2-naphthyl)-4-hydroxy-but-3-en-2-one (3 g) was hydrogenated at atmospheric pressure and room temperature in glacial acetic acid (150 ml) using 10% palladium on carbon (0.5 g) catalyst. When hydrogen uptake had ceased the catalyst was removed by filtration and the filtrate concentrated. The residue was taken up in ether and the resulting solution washed with sodium bicarbonate solution, then water, dried ($MgSO_4$) and concentrated in vacuo to give a low melting solid which was recrystallised from ether to give colourless crystals (1.40 g) m.p. 69°–70° C. 'H Nmr ($CDCl_3$)δ: 6.81–7.71 (m, 5H), 3.89 (s, 3H), 2.88–2.99 (m, 4H), 2.12 (s, 3H).

The compound of this example was found to be active at a dose of 10 mg/kg on the rat cotton pellet test (in the same test 4-(6-methoxy-2-naphthyl)butan-2-one was active at a dose of 20 mg/kg). No overt toxic effects were seen with the test compound.

EXAMPLE 4

4-(4-Fluoro-6-methoxy-2-naphthyl)-pent-3-en-2-one 1,2-Dimethyoxyethane (distilled from lithium aluminium hydride) (14 ml) was added to sodium hydride (4 g) (prepared by washing a dispersion in oil with dry ether) under a nitrogen atmosphere. Triethylphosphonoacetate (33 g) was added dropwise while the stirred suspension was cooled in an ice-bath. 1,2-Dimethoxyethane (78 ml, ex.LAH) and 2-acetyl-4-fluoro-6-methoxynaphthalene (20 g) in 1,2-dimethoxyethane (210 ml, ex. LAH) were added. The stirred mixture was heated under reflux for 16 hours. The mixture was then cooled in an ice-bath and water (450 ml) was added. After acidification with concentrated hydrochloric acid the mixture was extracted with ether. The ether solution was washed with sodium carbonate solution and water and was dried over anhydrous sodium sulphate. Removal of the solvent under reduced pressure gave a dark oil which solidified on standing to give ethyl 3-(4-fluoro-6-methoxy-2-naphthyl)-but-3-enoate as yellow crystals (22.2 g., 84%; m.p. 50°–52°).

NMR ($CDCl_3$), (δ) 7.8–6.9 (m, 5H, Ar-$\underline{H}$), 6.20 (m, 1H, =C$\underline{H}$—$CO_2$Et), 4.22 (q, 2H, —O—C$\underline{H}_2$—$CH_3$), 3.88 (s, 3H, —O—$CH_3$), 2.6 (m, 3H, Ar—C(—$CH_3$)=CH—), 1.30 (t, 3H, —O—$CH_2$—$CH_3$); IR (Nujol) ($CM^{-1}$) 1720 (>C=O).

The ethyl ester (10 g) was heated under reflux for 2 hours with methanol (200 ml) and 10% aqueous sodium hydroxide solution (100 ml). The solution was then cooled and poured into water (300 ml). The suspension produced was acidified with hydrochloric acid and the precipitate was extracted into ethyl acetate. After drying over anhydrous sodium sulphate the solvent was removed under reduced pressure to give a crude product. Recrystallisation from ethyl acetate gave 3-(4-fluoro-6-methoxy-2-naphthyl)-but-2-enoic acid as pale yellow crystals (7.05 g., 78%; m.p. 214°–217°).

NMR (DMSO-$d_6$), (δ) 8.1–7.1 (m, 5H, Ar-$\underline{H}$), 6.3 (m, 1H, C=C$\underline{H}$—$CO_2$H), 3.92 (s, 3H, Ar—C(—$\underline{CH_3}$)=CH—); IR (Nujol) ($cm^{-1}$) 3300–2500 (broad absorption), 1710 (>C=O).

The acid (7.5 g) and thionyl chloride (3.0 ml) were heated under reflux in benzene (80 ml) for 16 hours. The benzene and excess thionyl chloride were then removed by evaporation under reduced pressure. Dry tetrahydrofuran (70 ml) was added to copper (I) iodide (18.39 g) under a nitrogen atmosphere. The suspension obtained was cooled to 0°. Methyl lithium (108 ml of a 1.77 M solution in ether) was added slowly to the stirred suspension. When addition was complete the solution was cooled to −78° and the crude chloride in dry tetrahydrofuran (70 ml) was added dropwise. The mixture was stirred at −78° for 15 minutes after addition was complete. Methanol (15 ml) was then added and the mixture was allowed to warm to room temperature. Water (190 ml) was added and the mixture was acidified with concentrated hydrochloric acid. The resulting suspension was filtered through a celite bed. The residue was washed with ether and the washings were combined with the filtrate. The organic layer was separated and washed with sodium carbonate solution and water. The organic solution was dried over anhydrous sodium sulphate and the solvent was removed under reduced pressure. The solid obtained was dissolved in benzene and boiled with charcoal. The suspension was filtered through a celite bed and the solvent was removed under reduced pressure. The solid obtained was crystallised from methanol. After further treatment with charcoal, crystallisation from methanol gave the title compound as yellow crystals (4.8 g. 64%; m.p. 126°–127°).

NMR ($CDCl_3$) (δ) 7.9–7.0 (m, 5H, Ar-$\underline{H}$), 6.6 (m, 1H, =C$\underline{H}$—CO—), 3.95 (s, 3H, —O—$\underline{CH_3}$), 2.60 (s, 3H, Ar—C(—$\underline{CH_3}$)=CH—), 2.31 (s, 3H, —CO—$\underline{CH_3}$); IR (Nujol) ($cm^{-1}$) 1710, 1680; Anal. (Reqd.) C, 74.45 (74.40); H, 5.90 (5.85); F, 7.39 (7.36).

EXAMPLE 5

4-(4-Fluoro-6-methoxy-2-naphthyl)-pentan-2-one

Ethyl 3-(4-fluoro-6-methoxy-2-naphthyl)-but-2-enoate (12 g) was dissolved in ethyl acetate (100 ml) and 5% palladium on charcoal (1.5 g) was added. The mixture was shaken under a hydrogen atmosphere until uptake of hydrogen ceased (ca. 1 hour). The catalyst was removed by filtration through a celite bed and the solvent was removed under reduced pressure to give ethyl 3-(4-fluoro-6-methoxy-2-naphthyl)-butanoate as an oil (11.9 g., 98%).

NMR ($CDCl_3$) (δ) 7.8–6.9 (m, 5H, Ar-$\underline{H}$), 4.10 (q, 2H, —O—C$\underline{H}_2$—$CH_3$), 3.90 (s, 3H, —O—$CH_3$), 3.40 (m, 1H, Ar—C$\underline{H}$($CH_3$)—$CH_2$—), 2.60 (m, 2H, >CH—C$\underline{H}_2$—$CO_2$Et), 1.35 (d, 3H, Ar—CH(—$\underline{CH_3}$)—$CH_2$—), 1.15 (t, 3H, —O—$CH_2$—$\underline{CH_3}$); IR (liquid film) ($cm^{-1}$) 3100–2800, 1730 (>C=O), 1615.

The ester (9 g) was dissolved in methanol (180 ml) and 10% aqueous sodium hydroxide solution (90 ml) was added. The solution was heated under reflux for 2 hours. It was then poured into water (270 ml) and the suspension was acidified with dilute hydrochloric acid. The precipitate produced was extracted into ethyl acetate. The organic solution was dried over anhydrous sodium sulphate and the solvent was removed under reduced pressure to give 3-(4-fluoro-6-methoxy-2-naphthyl)butanoic acid as an oil which crystallised on standing (12.4 g., >100%).

NMR (DMSO-$d_6$) (δ) 8.0–7.1 (m, 5H, Ar-$\underline{H}$), 3.88 (s, 3H, —O—$\underline{CH_3}$), 3.35 (m, 1H, Ar—C$\underline{H}$(—$CH_3$)—$CH_2$—), 2.65 (m, 2H, >CH—C$\underline{H}_2$—$CO_2$H), 1.30 (d, Ar—CH(—$\underline{CH_3}$)—$CH_2$—); IR (Nujol) ($cm^{-1}$) 3300–2500 (broad absorption), 1710 (>C=O), 1640, 1615.

The crude acid (11.5 g) was dissolved in benzene (140 ml). Thionyl chloride (4.7 ml) was added and the mixture was heated under reflux for 16 hours. After slight cooling the solvent was removed under reduced pressure to give the crude acid chloride. Dry tetrahydrofuran (110 ml) was added to copper (I) iodide (28.2 g) under a nitrogen atmosphere. The suspension was cooled to 0° and methyl lithium (166 ml of a 1.77 M solution in ether) was added slowly with stirring. When addition was complete the solution was cooled to −78° and the crude acid chloride in dry tetrahydrofuran (110 ml) was added dropwise. The mixture was stirred at −78° for 15 minutes after addition was complete. Methanol (22 ml) was then added and the mixture was warmed to room temperature. Water (290 ml) was added and the mixture was acidified with concentrated hydrochloric acid. The resulting suspension was filtered through a celite bed. The residue was washed with ether and the washings were combined with the filtrate. The organic layer was separated and washed with sodium carbonate solution and water. The solution was dried over anhydrous sodium sulphate and the solvent was removed under reduced pressure to give an oil. This was treated with charcoal in benzene and after the charcoal had been removed by filtration through a celite bed the solvent was removed under reduced pressure to give an oil. This was triturated with cold 60–80 petroleum ether to give a crystalline product. This was recrystallised twice from cold methanol to give the title compound as pale yellow crystals (3.8 g., 33%; m.p. 38°–39°).

NMR (CDCl$_3$) ($\delta$) 7.9–6.9 (m, 5H, Ar-H), 3.95 (s, 3H, —O—CH$_3$), 3.48 (m, 1H, Ar—CH(—CH$_3$)—CH$_2$—), 2.80 (m, 2H, CH—CH$_2$—CO), 2.08 (s, 3H, —CO—CH$_3$), 1.35 (d, 3H, Ar—CH(—CH$_3$)—CH$_2$—); IR (liquid film) (cm$^{-1}$) 3100–2800, 1715 (>C=O), 1610; Anal. Reqd.) C, 73.61 (73.83); H, 6.74 (6.58); F, 6.90 (7.30).

EXAMPLE 6

4-(4-Fluoro-6-methoxy-2-naphthyl)butan-2-ol 4-(4-Fluoro-6-methoxy-2-naphthyl)butan-2-one (14.1 g) was dissolved in ethanol (200 ml) and sodium borohydride (6.7 g) was added to the stirred solution. After 1 hour ether (600 ml) was added and the solution was washed twice with brine, then with dilute hydrochloric acid and sodium hydrogen carbonate solution. After drying over anhydrous sodium sulphate the solvent was removed under reduced pressure. The oil obtained was chromatographed on silica gel (700 g) using an elution gradient from benzene to ether. The desired product was obtained as an oil. This was triturated with 60–80 petroleum ether to give the title compound as pale yellow crystals (5.65 g., 40%; m.p. 58°–60°).

NMR (CDCl$_3$) ($\delta$) 7.8–6.9 (m, 5H, Ar-H), 3.95 (s, 3H, —O—CH$_3$), 3.85 (m, 1H, —CH$_2$—CH(OH)—CH$_3$), 2.88 (m, 2H, Ar—CH$_2$—CH$_2$—), 1.80 (m, 2H, —CH$_2$—CH$_2$—CH(OH)—), 1.70 (b.s., 1H, removed by shaking with D$_2$O, —O—H), 1.25 (d, 3H, —CH(—OH)—CH$_3$); IR (Nujol) (cm$^{-1}$) 3450 (broad) 1615; Anal. (Reqd.) C, 72.53 (72.85); H, 7.00 (6.93); F, 7.79 (7.28).

EXAMPLE 7

4-(4-Fluoro-6-methoxy-2-naphthyl)-but-2-yl acetate 4-(4-Fluoro-6-methoxy-2-naphthyl)-butan-2-ol (2.8 g) was dissolved in pyridine (22 ml) and cooled in an ice-bath. Acetyl chloride (2.9 ml) was added dropwise with stirring. The solution was then stirred for 30 minutes at 0° and 1 hour at room temperature. The suspension produced was poured into ice-water (250 ml) and the product was extracted into ether. The ether was washed with dilute hydrochloric acid and sodium hydrogen carbonate solution. After drying over anhydrous sodium sulphate and solvent was removed under reduced pressure to give the title compound as a pale yellow oil (2.8 g., 85%).

NMR (CDCl$_3$) ($\delta$) 7.8–6.8 (m, 5H, Ar-H), 4.95 (m, 1H, —CH$_2$—CH(OAc)—CH$_3$), 3.88 (s, 3H, —O—CH$_3$), 2.75 (m, 2H, Ar—CH$_2$—CH$_2$—), 2.00 (s, 3H, —CO—CH$_3$), 1.95 (m, 2H, —CH$_2$—CH$_2$—CH(OAc)—), 1.25 (d, 3H, —CH(OAc)—CH$_3$); IR (liquid film) (cm$^{-1}$) 3100–2800, 1740 (C=O), 1615; Anal. (Reqd.) C, 70.28 (70.33); H, 6.68 (6.60); F, 6.48 (6.54).

EXAMPLE 8

2-[2-(4-Fluoro-6-methoxy-2-naphthyl)-ethyl]-2-methyl-1,3-dioxolane 4-(4-Fluoro-6-methoxy-2-naphthyl)butan-2-one (4.2 g), ethane-1,2-diol (30 ml) and toluene-4-sulphonic acid (0.2 g) were heated under reflux in benzene for 18 hours with continuous removal of water by means of a Dean-Stark trap. The solution was then cooled to room temperature and sodium hydrogen carbonate solution was added. The aqueous layer was washed with ether. The combined organic layers were washed with water and dried over anhydrous sodium sulphate. Evaporation of the solvent under reduced pressure gave a crude product which was dissolved in 60–80 petroleum ether. The precipitated impurities were removed by filtration and the solvent was removed under reduced pressure to give a yellow oil which was triturated with cold 40–60 petroleum ether to give the title compound as pale yellow crystals (2.6 g., 53%; m.p. 51°–53°).

NMR (CDCl$_3$) ($\delta$) 7.8–6.9 (m, 5H, Ar-H), 3.98 (s, 3H, —O—CH$_3$), 3.91 (s, 4H, —O—CH$_2$—CH$_2$—O—), 2.85 (m, 2H, Ar—CH$_2$—CH$_2$—), 2.02 (m, 2H, Ar—CH$_2$—CH$_2$—), 1.38 (s, 3H, CH$_3$—C(—OCH$_2$)$_2$—CH$_2$—); IR (Nujol) (cm$^{-1}$), 1615; Anal. (Reqd.) C, 70.51 (70.33); H, 6.45 (6.60).

EXAMPLE 9

Pharmaceutical Compositions 4-(4'-Fluoro-6'-methoxy-2'-naphthyl)butan-2-one (500 mg) may be filled into a two part hard gelatin capsule. Such a capsule may be used for oral administration.

DESCRIPTION 1

1-Fluoro-7-methoxynaphthalene

A vigorously stirred suspension of 7-methoxy-1-naphthylamine hydrochloride (30.8 g) in concentrated hydrochloric acid (60 ml) and water (94 ml) was cooled in an ice bath. (Internal temperature >5° C.). A solution of sodium nitrite (13.4 g) in 50 ml water was added dropwise, and when addition was complete the reaction mixture was stirred for 15 minutes at >5° C. Hexafluorophosphoric acid (77 ml of 65% solution) was added rapidly and the resulting yellow solid was removed by filtration, washed with water and dried to constant weight at room temperature (36.52 g) m.p. 128°–130° C. dec.

The salt was added in small portions to dry xylene (1½ liters) stirring at 140° C. (external temperature, i.e. just below b.pt.), and a vigorous evolution of nitrogen and phosphorus pentafluoride ensued. Stirring was continued after the addition was complete until gas evolution had ceased (approx. 20 minutes). The mixture was then rapidly cooled, washed with sodium carbonate solution, then water, dried and concentrated to give a red oil (21.2 g). This was purified on a silica gel column using petroleum ether 95%/ether 5% to yield a pale yellow oil (13 g).

2-Acetyl-4-fluoro-6-methoxynaphthalene

A mixture of 1-fluoro-7-methoxynaphthalene (13 g) and acetyl chloride (8.0 g) in nitrobenzene (120 ml), cooled in an ice bath, was treated with anhydrous aluminium chloride (15.6 g) over a period of 20 minutes. The reaction mixture was then stirred at room temperature overnight. Dilute hydrochloric acid (150 ml) was then carefully added to the cooled mixture and the resulting mixture steam distilled to remove nitrobenzene (some product also distils but remains in the condenser). After cooling, the residue was extracted several times with ether and the extracts combined, washed with water, dried and concentrated to give a brown solid which was purified by column chromatography on silica gel using petroleum ether 50%/ether 50%. Recrystallisation from ether gave 5.33 g colourless solid m.p. 96°-7° C.

What we claim is:

1. A compound of the formula:

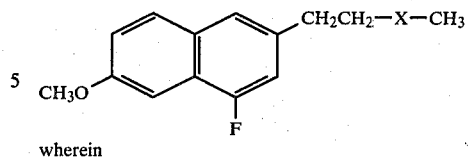

wherein

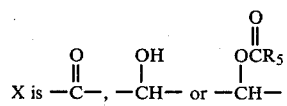

wherein $R_5$ is alkyl of from 1 to 4 carbon atoms.

2. The compound according to claim 1 which is 4-(4-fluoro-6-methoxy-2-naphthyl)butan-2-one.

3. The compound according to claim 1 which is 4-(4-fluoro-6-methoxy-2-naphthyl)butan-2-ol.

4. The compound according to claim 1 which is 2-acetoxy-4-(4-fluoro-6-methoxy-2-naphthyl)butane.

5. A pharmaceutical composition which comprises an antiinflammatory effective amount of a compound according to claim 1 and a pharmaceutically acceptable carrier therefor.

6. A composition according to claim 5 in shaped unit dosage form adapted for oral administration which comprises from 20 mg to 1000 mg of a compound as therein defined.

7. A method of treatment of an inflammatory disease which comprises administering to an animal in need thereof an anti-inflammatorily effective amount of a compound according to claim 1.

8. A composition according to claim 6 wherein said compounds is 4-(4-fluoro-6-methoxy-2-naphthyl)butan-2-one, the amount of which in said composition is from 50 to 600 mg.

* * * * *